(12) United States Patent
Wang et al.

(10) Patent No.: US 7,572,930 B2
(45) Date of Patent: Aug. 11, 2009

(54) PROCESS FOR PREPARING 1-(MERCAPTOMETHYL) CYCLOPROPANEACETIC ACID, A USEFUL INTERMEDIATE IN THE PREPARATION OF MONTELUKAST AND SALTS THEREOF

(75) Inventors: Yanling Wang, Shanghai (CN); Yuang Wang, Shanghai (CN); Michael Brand, RaAnana (IL); Joseph Kaspi, Givatayim (IL)

(73) Assignee: Chemagis Ltd., Bnei-Brak (IL)

( * ) Notice: Subject to any disclaimer, the term of this patent is extended or adjusted under 35 U.S.C. 154(b) by 399 days.

(21) Appl. No.: 11/700,867

(22) Filed: Feb. 1, 2007

(65) Prior Publication Data

US 2007/0208177 A1    Sep. 6, 2007

Related U.S. Application Data

(60) Provisional application No. 60/764,347, filed on Feb. 2, 2006.

(51) Int. Cl.
*C07C 255/01* (2006.01)
(52) U.S. Cl. ...................... 558/434; 558/303
(58) Field of Classification Search ............... 558/303, 558/434
See application file for complete search history.

(56) References Cited

U.S. PATENT DOCUMENTS 5,614,632 A    3/1997    Bhupathy et al.
6,512,140 B1    1/2003    Liu et al.

FOREIGN PATENT DOCUMENTS

EP           480717        4/1992
WO    WO 2007/088545    8/2007

*Primary Examiner*—Golam M Shameem

(57) ABSTRACT

The present invention provides a novel montelukast intermediate and a simple and straightforward process for preparing it.

According to the present invention, by using this intermediate and the process, essentially as described herein, montelukast acid and salts thereof are obtained.

3 Claims, No Drawings

PROCESS FOR PREPARING 1-(MERCAPTOMETHYL) CYCLOPROPANEACETIC ACID, A USEFUL INTERMEDIATE IN THE PREPARATION OF MONTELUKAST AND SALTS THEREOF

RELATED APPLICATIONS

The present application claims the benefit of U.S. Provisional Patent Application No. 60/764,347 filed on Feb. 2, 2006, which is incorporated herein by reference.

FIELD OF THE INVENTION

The field of the invention relates to organic chemistry and more particularly to novel synthetic process and novel intermediate for preparing the side-chain precursor 1-(mercaptomethyl)cyclopropaneacetic acid, which is useful in the synthesis of montelukast and salts thereof.

BACKGROUND OF THE INVENTION (R-(E)-1-(((1-(3-(2-(7-chloro-2-quinolinyl)ethenyl)phenyl)-3 -(2-(1-hydroxy-1-methylethyl)phenyl)propyl)thio) methyl)cyclopropaneacetic acid sodium salt, also known by the name montelukast sodium, is represented by the structural formula I below:

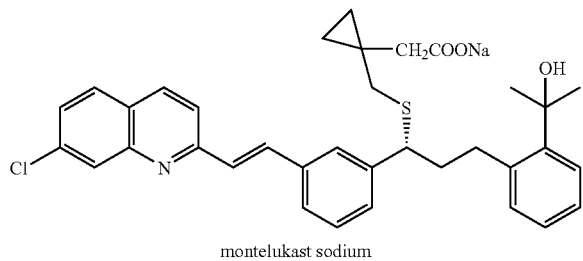

montelukast sodium

Montelukast sodium is a leukotriene antagonist, and is thus useful as an anti-asthmatic, anti-allergic, anti-inflammatory and cytoprotective agent. Montelukast sodium is currently indicated for the treatment of asthma and allergic rhinitis.

Montelukast sodium, formulated as tablets (containing 10.4 mg montelukast sodium), chewable tablets (containing 4.2 or 5.2 mg montelukast sodium) or oral granules (in a packet containing 4.2 mg montelukast sodium), is typically given once daily to the patients for the treatment of asthma and seasonal allergic rhinitis. Montelukast sodium is marketed in the United States and other countries by Merck & Co., Inc. under the trade name Singulair®.

Montelukast sodium and related compounds were first disclosed in European Patent No. EP 480,717. The synthesis of montelukast sodium, as taught in patent EP 480,717, involves coupling methyl 1-(mercaptomethyl)cyclopropaneacetate with (S)-1-(3-(2-(7-chloro-2-quinolinyl)ethenyl(phenyl)-3(-2-(1-hydroxy-1-methylethyl)-phenyl)propyl) methanesulfonate, followed by hydrolysis of the resulting methyl ester so as to form a free acid, which is followed by conversion of the free acid into a corresponding sodium salt.

U.S. Pat. No. 5,614,632 (hereinafter the '632 patent) teaches a method of preparing crystalline montelukast sodium, which involves the preparation of the dilithium dianion of 1-(mercaptomethyl)cyclopropaneacetic acid as an intermediate, followed by condensation thereof with 2-(2-(3-(S)-(3-(7-chloro-2-quinolinyl ethenyl)phenyl)-3-methanesulfonyloxypropyl)phenyl)-2-propanol, to yield montelukast acid. This process comprises converting 1-(mercaptomethyl)-cyclopropaneacetic acid into a dilithium dianion by reaction with lithium bases such as n-butyl lithium in a solvent mixture at low temperature and reacting the dilithium dianion of 1-(mercaptomethyl)cyclopropaneacetic acid with the mesylate intermediate, mentioned earlier, which has limited stability and is therefore prepared in situ. Thus, upon coupling of the mesylate 2-(2-2(3(S)-(3-(2-(7-chloro-2-quinolinyl)ethenyl)phenyl)-3-methanesulfonyloxy propyl) phenyl)-2-propanol with the dilithium dianoin, montelukast acid is obtained as a viscous oil. The resulting montelukast acid is converted, via the corresponding dicyclohexyl ammonium salt, into montelukast sodium.

The '632 patent describes also a process for preparing the side-chain precursor 1-(mercaptomethyl)cyclopropaneacetic acid, which is depicted in Scheme 1 below.

Scheme 1

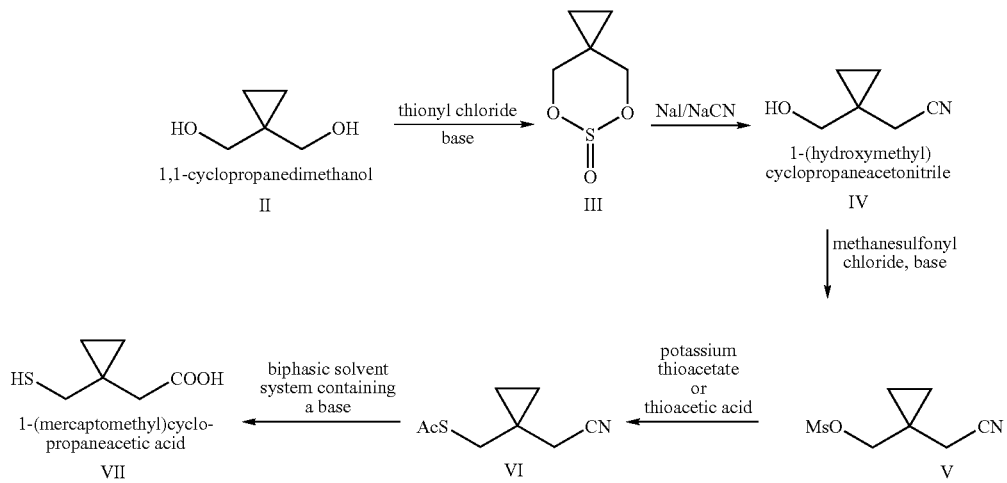

The first step comprises converting the starting material 1,1-cyclopropanedimethanol II into the corresponding cyclic sulfite III by using thionyl chloride and in the presence of a base such as diisopropylethylamine. The cyclic sulfite III is treated with catalytic amount of sodium iodide and sodium cyanide to obtain the compound 1-(hydroxymethyl)cyclopropaneacetonitrile IV, which is converted into the corresponding mesylate 1-(methanesulfonyloxymethyl)-cyclopropaneacetonitrile V, by using methanesulfonyl chloride in the presence of a base. Compound V is treated with potassium thioacetate or thioacetic acid in the presence of a base to yield the compound 1-(acetylthiomethyl)-cyclopropaneacetonitrile VI. In the last step, compound VI is converted into 1-(mercaptomethyl)cyclopropaneacetic acid VII by reacting compound VI in a biphasic solvent system comprising toluene and aqueous NaOH for 16-18 hours.

The intermediate 1-(mercaptomethyl)cyclopropaneacetic acid is not stable and is being prone to oxidation like many other thiols, as generally depicted in Scheme 2 below.

Scheme 2

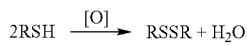

This is evident from example 4 of the '632 patent, which tackles the instability problem of 1-(mercaptomethyl)cyclopropaneacetic acid by carrying out the reaction under nitrogen. In addition, the use of sodium cyanide or thioacetic acid is unfavorable on industrial scale because of high toxicity or pungent odor.

U.S. Pat. No. 6,512,140 (hereinafter the '140 patent) provides a process for preparing the compound 1-(mercaptomethyl)cyclopropaneacetic acid, which is described in Scheme 3 below.

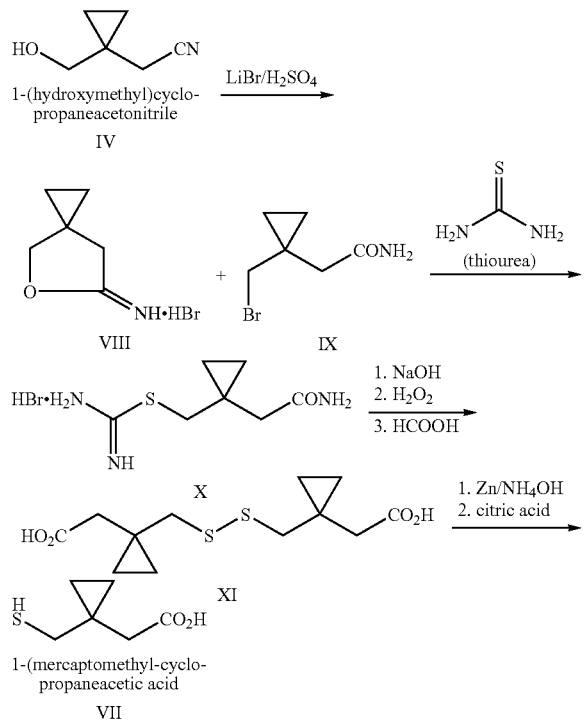

The process comprises reacting 1-(hydroxymethyl)cyclopropaneacetonitrile IV with an acid, to thus obtain the corresponding mixture of cyclic imino ether and halo-amide (VIII and IX respectively), which when reacted with thiourea provides the corresponding amide-isothiuronium salt X. Hydrolysis of the amide-isothiuronium salt X followed by an in situ oxidation affords the intermediate 1-(mercaptomethyl) cyclopropaneacetic acid disulfide XI, which affords the final product upon treatment with a solution containing ammonium hydroxide and metal zinc for 3.5 hours followed by treatment with citric acid. Thus, the oxidation problem of the corresponding amide was solved by dimerizing the thiolamide, which may yield the requested product by reduction. However, the problem with the process provided in the '140 patent is that it is lengthy and contains laborious procedures.

Unstable intermediates such as 1-(mercaptomethyl)cyclopropaneacetic acid (and the need to use special reaction conditions thereof) are not easily amendable to industrial scale production. Hence, there is still a need in the art for a side-chain precursor that is stable on one hand, and which may be more conveniently prepared and used in the synthesis of montelukast sodium on the other hand.

SUMMARY OF THE INVENTION

The present invention provides a novel side-chain precursor of montelukast sodium, and a process for its preparation thereof.

In search for a stable side-chain precursor, as explained herein, the inventors of the present invention have surprisingly uncovered an alternative simple novel synthetic process for preparing the compound 1-(mercaptomethyl)cyclopropaneacetic acid VII starting from 1-(hydroxymethyl)cyclopropaneacetonitrile IV, which is commercially available.

The process provided by the present invention for preparing the side-chain precursor 1-(mercaptomethyl)cyclopropaneacetic acid VII is simple and straightforward and in addition it provides the compound 1-(isothiuroniummethyl) cyclopropaneacetonitrile salt (e.g. hydrobromide, hydrochloride or hydroiodide salt), which is a crystalline stable compound that may be stored at room temperature for extended periods. When needed is it treated with a base to obtain the compound 1-(mercaptomethyl)cyclopropaneacetic acid. The thiol acid VII may be directly reacted without isolation with the mesylate 2-(2-2(3(S)-(3-(2-(7-chloro-2-quinolinyl)ethenyl)phenyl)-3-methanesulfonyloxypropyl) phenyl)-2-propanol XIV to yield montelukast and salts thereof.

Thus, the present invention provides a process for preparing the side-chain precursor 1-(mercaptomethyl)cyclopropaneacetic acid, the process preferably includes:

preparing the intermediate 1-(bromomethyl)cyclopropaneacetonitrile;

converting the intermediate 1-(bromomethyl)cyclopropaneacetonitrile into the compound 1-(isothiuroniummethyl)cyclopropaneacetonitrile salt; and reacting the compound 1-(isothiuroniummethyl)-cyclopropaneacetonitrile salt with a base to obtain 1-(mercaptomethyl)-cyclopropaneacetic acid or its salts thereof.

The reaction product 1-(mercaptomethyl)cyclopropaneacetic acid may be optionally reacted in situ with the mesylate 2-(2-2(3(S)-(3-(2-(7-chloro-2-quinolinyl)ethenyl)phenyl)-3-methanesulfonyloxypropyl)phenyl)-2-propanol XIV to obtain moltelukast and its salts thereof.

According to the present invention, preparing the intermediate 1-(bromomethyl)cyclopropaneacetonitrile preferably includes:

reacting 1-(hydroxymethyl)cyclopropaneacetonitrile with bromine in the presence of an organic phosphine in an organic solvent, optionally at elevated temperature; and optionally isolating the product.

Preparing the intermediate 1-(isothiuroniummethyl)cyclopropaneacetonitrile salt preferably includes:

reacting 1-(bromomethyl)cyclopropaneacetonitrile with thiourea in an organic solvent, optionally at elevated temperature; and optionally isolating the product Preparing the compound 1-(mercaptomethyl)cyclopropaneacetic acid preferably includes:

reacting 1-(isothiuroniummethyl)cyclopropaneacetonitrile salt with a base, optionally at elevated temperature;

optionally isolating the product; and optionally purifying the product by crystallization.

DETAILED DESCRIPTION OF THE INVENTION

While preparing the compound 1-(mercaptomethyl)cyclopropaneacetic acid, the inventors of the present invention have encountered that this compound is not stable and that it is being prone to oxidation, even by exposure to air, hence the reaction had to be carried out using degassed solvents and reagents (see example 3 of the present invention). Furthermore, in order to test the stability of the compound 1-(mercaptomethyl)cyclopropaneacetic, it was stored in the refrigerator for a period of up to 6 months. The substance was packed in a clear sealed polyethylene bag, which was inserted into a black polyethylene bag. The black sealed polyethylene bag was inserted into an aluminum bag, which was sealed and stored in a closed fiber drum. It has been found that during the above mentioned storage period, the purity of the compound dropped from 98.1% to 97.6% (by HPLC), hence it may concluded that even at strict storing conditions the material has limited stability.

In a search for a more stable side-chain precursor, as explained herein, the inventors of the present invention have surprisingly uncovered an alternative novel synthetic process for preparing the compound 1-(mercaptomethyl)cyclopropaneacetic acid VII starting from 1-(hydroxymethyl)cyclopropaneacetonitrile IV, which is commercially available. Therefore, the present invention provides a novel side-chain precursor of montelukast sodium, and a process for its preparation thereof, which is depicted in Scheme 4 below.

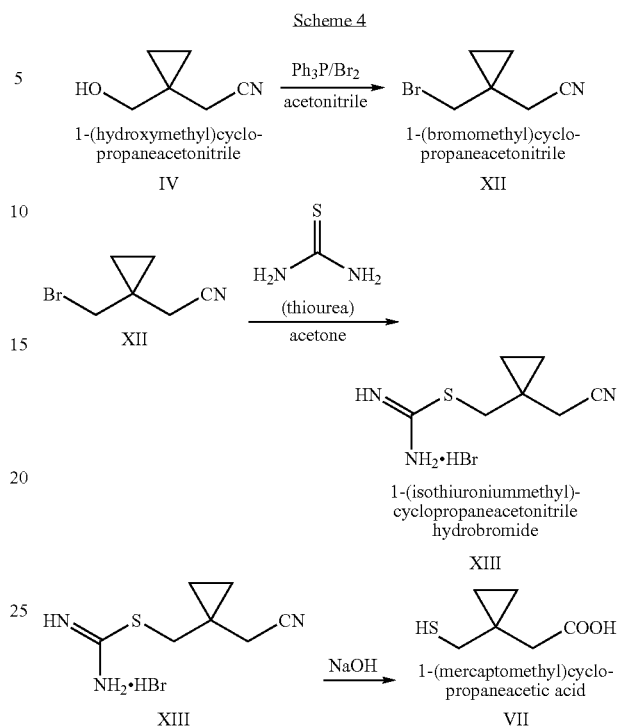

According to the present invention, the process, which is depicted in Scheme 4, is simple and straightforward and in addition it provides the novel compound 1-(isothiuroniummethyl)cyclopropaneacetonitrile salt XIII (e.g. hydrobromide, hydrochloride or hydroiodide salt), which is a crystalline stable compound that may be stored at room temperature for extended period of time prior to treatment with a base, when it is needed, to obtain the compound 1-(mercaptomethyf) cyclopropaneacetic acid, optionally in situ, followed by reacting the thus formed side-chain precursor with the mesylate 2-(2-2(3(S)-(3-(2-(7-chloro-2-quinolinyl)ethenyl)phenyl)-3-methanesulfonyloxypropyl)-phenyl)-2-propanol XIV to yield montelukast and salts thereof.

The process for preparing montelukast and salts thereof using the compound 1-(mercaptomethyl)cyclopropaneacetic acid is provided in Scheme 5 below. The process comprises reacting 1-(mercaptomethyl)cyclopropaneacetic acid VII and the mesylate 2-(2-2(3(S)-(3-(2-(7-chloro-2-quinolinyl)ethenyl)phenyl)-3-methane-sulfonyloxyropyl)phenyl)-2-propanol XIV, e.g., as per example 4 of the present invention.

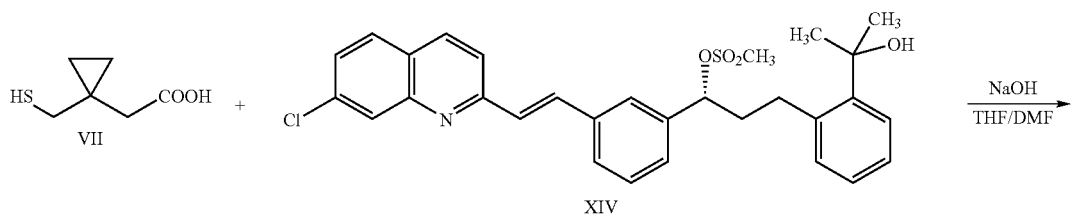

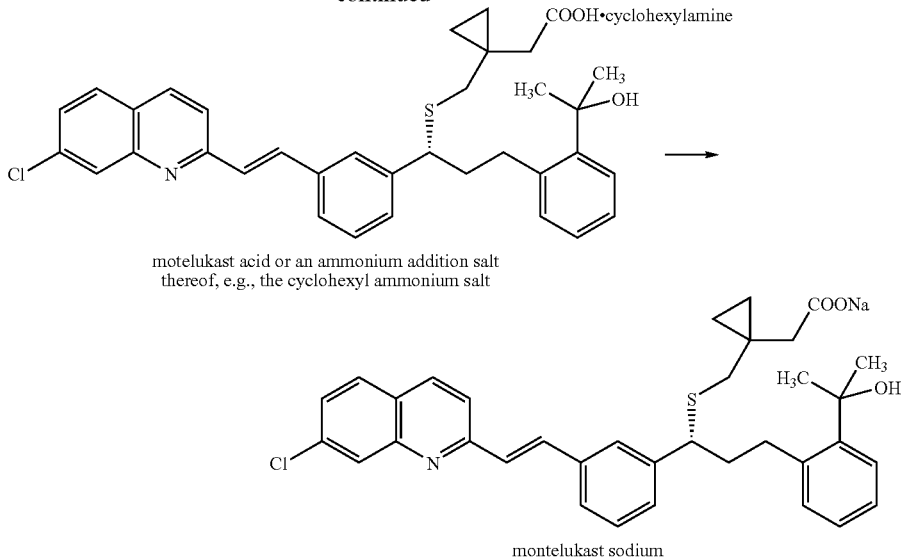

motelukast acid or an ammonium addition salt thereof, e.g., the cyclohexyl ammonium salt montelukast sodium Thus, the present invention provides a process for preparing the side-chain precursor 1-(mercaptomethyl)cyclopropaneacetic acid, the process preferably includes:
  preparing the intermediate 1-(bromomethyl)cyclopropaneacetonitrile;
  converting the intermediate 1-(bromomethyl)cyclopropaneacetonitrile into the compound 1-(isothiuroniummethyl)cyclopropaneacetonitrile salt XIII; and
  reacting the compound XIII with a base to obtain 1-(mercapto-methyl)cyclopropaneacetic acid or its salts thereof.

The reaction product 1-(mercaptomethyl)cyclopropaneacetic acid may be optionally reacted in situ with the mesylate XIV to obtain moltelukast acid and addition salts thereof.

According to the present invention, preparing the intermediate 1-(bromomethyl)cyclopropaneacetonitrile preferably includes:
  reacting 1-(hydroxymethyl)cyclopropaneacetonitrile with bromine in the presence of an organic phosphine in an organic solvent, optionally at elevated temperature;
  optionally cooling the reaction mixture and obtaining a cake by filtration; and
  washing the cake with organic solvents and drying.

Preferably, the organic phosphine is a tertiary phosphine selected from the group consisting of tri-n-butyl phosphine, tri-t-butyl phosphine, tricyclohexylphosphine, trioctylphosphine, triphenylphosphine, tri-o-tolylphosphine, cyclohexyldiphenylphosphine, dicyclohexylphenylphosphine, and the like, more preferably triphenylphosphine.

The solvent used for conducting the reaction is preferably selected from the group consisting of acetonitrile, tetrahydrofuran (THF), 2-methyltetrahydrofuran, N,N-dimethylformamide (DMF), diethyl ether, diisopropyl ether, methyl t-butyl ether (MTBE), and mixtures thereof, more preferably acetonitrile.

The solvents used for washing the obtained cake are preferably selected from the group consisting of acetonitrile, acetone, methyl acetate, ethyl acetate, n-propyl acetate, isopropyl acetate, n-butyl acetate, isobutyl acetate, diethyl ether, diisopropyl ether, methyl t-butyl ether (MTBE), and the like, and mixtures thereof, more preferably acetonitrile and methyl t-butyl ether (MTBE).

According to the present invention, preparing the intermediate 1-(isothiuroniummethyl)cyclopropaneacetonitrile salt XIII preferably includes:
  reacting 1-(bromomethyl)cyclopropaneacetonitrile with thiourea in an organic solvent, optionally at elevated temperature;
  optionally cooling the reaction mixture and obtaining a cake by filtration; and
  washing and/or slurrying the cake in an organic solvent and drying.

According to the present invention, the 1-(isothiuroniummethyl)-cyclopropaneacetonitrile salt is e.g., the hydrobromide salt, or the hydrochloride salt, or the hydroiodide salt, preferably the hydrobromide salt.

The reaction solvent is preferably selected from the group consisting of acetonitrile, acetone, methyl acetate, ethyl acetate, n-propyl acetate, isopropyl acetate, n-butyl acetate, isobutyl acetate, diethyl ether, diisopropyl ether, methyl t-butyl ether (MTBE), and the like, and mixtures thereof, more preferably acetone.

The solvent used for washing the obtained cake is preferably selected from the group consisting of acetonitrile, acetone, methyl acetate, ethyl acetate, n-propyl acetate, isopropyl acetate, n-butyl acetate, isobutyl acetate, diethyl ether, diisopropyl ether, methyl t-butyl ether (MTBE) and the like, and mixtures thereof, more preferably acetone.

According to the present invention, preparing the side-chain precursor 1-(mercaptomethyl)cyclopropaneacetic acid preferably includes:
  reacting the compound 1-(isothiuroniummethyl)cyclopropaneacetonitrile salt XIII with a base, optionally at elevated temperature;
  optionally cooling the reaction mixture and adding an organic solvent;
  acidifying the mixture with an acid and separating the layers;

washing the organic layer and drying; and
optionally purifying the product by crystallization.

Preferably, the base is selected from the group consisting of lithium hydroxide, sodium hydroxide, potassium hydroxide, cesium hydroxide, and the like, more preferably sodium hydroxide.

Preferably, the organic solvent is selected from the group consisting of methyl acetate, ethyl acetate, n-propyl acetate, isopropyl acetate, n-butyl acetate, isobutyl acetate, dichloromethane, chloroform, and mixtures thereof, more preferably ethyl acetate.

The solvent used for purifying by crystallization is preferably selected from the group consisting of diethyl ether, diisopropyl ether, methyl t-butyl ether (MTBE), pentanes, hexanes, heptanes, cyclohexane, petrol ether, and the like, and mixtures thereof, more preferably hexanes.

The acid used for acidifying is an organic acid, which is preferably selected from the group consisting of formic acid, acetic acid, citric acid, tartaric acid, and the like, more preferably formic acid.

According to the present invention, all the solvents used in the process for obtaining the product 1-(mercaptomethyl)cyclopropaneacetic acid as well as the organic acid used for acidifying are degassed (to eliminate oxygen) in order to prevent oxidation of the product.

EXAMPLES

Reference is now made to the following examples, which together with the above descriptions, illustrate the invention in a non limiting fashion. Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Example 1

Preparation of
1-(bromomethyl)cyclopropane-acetonitrile

A 500 ml 3-necked flask equipped with a thermometer, a dropping funnel and a magnetic stirrer was charged with 74.8 g (0.28 mol) of $Ph_3P$ and 300 ml of acetonitrile, and was cooled to –8° C. under stirring. 43.2 g (0.27 mol) of bromine was added drop-wise at a temperature range of –10~0° C. The mixture was stirred at a temperature range of 0-5° C. until the yellow color disappeared. Then, 24.4 g (0.22 mol) of 1-(hydroxymethyl)cyclopropaneacetonitrile (IV) was added drop-wise at a temperature below 10° C. The reaction mixture was then heated to 60° C. for 15-20 minutes. The solution was cooled to a temperature below –10° C. for at least 1 hour and then the solution was filtered. The thus formed cake was washed with 2×100 ml of cold acetonitrile. The filtrate was concentrated to dryness and to the residue was added 100 ml of MTBE and the mixture was stirred at –8~3° C. for at least 1 hour. The mixture was then filtered and the thus formed cake was washed with 2×100 ml of cold MTBE. The filtrates were combined and concentrated. The washing step with MTBE was repeated twice, followed by drying the solid under vacuum to obtain 33.3 g of 1-(bromomethyl)cyclopropaneacetonitrile as an oil in 87% yield, having a purity of 97%.

$^1$HNMR ($CDCl_3$) δ 3.41 (s, 2H), 2.61 (s, 2H), 0.89 (m, 2H), 0.77 (m, 2H)

Example 2

Preparation of
1-(isothiuroniummethyl)cyclopropane-acetonitrile hydrobromide

A 500 ml round bottomed flask equipped with a condenser was charged with 32.6 g (0.187 mol) of 1-(bromomethyl)cyclopropaneacetonitrile, 165 ml of acetone and 14.4 g of thiourea and the mixture was stirred and heated to reflux for 12 hours. The reaction mixture was cooled to –8~3° C. and stirred for at least 1 hour and then filtered to obtain a cake, which was washed with 2×50 ml of cold acetone. Then, the vessel containing the cake was charged with 87 ml of acetone and slurried for 5 hours. The mixture was filtered and the thus formed cake was washed with 2×25 ml of cold acetone. After being dried under vacuum, 42.6 g of 1-(isothiuroniummethyl)cyclo-propaneacetonitrile hydrobromide was obtained as a white solid in 91.1% yield, having a purity of 99.2%, m.p. 156° C.

$^1$HNMR (DMSO-$d_6$) δ 9.22 (s, 2H), 9.06 (s, 1H), 3.38 (s, 2H), 2.73 (s, 2H), 0.70 (s, 4H); $^{13}$CNMR (DMSO-$d_6$) δ 169.57, 169.51, 38.46, 23.26, 16.71, 12.37; m/z: 170.1(M+ $H^+$).

Example 3

Preparation of
1-(mercaptomethyl)cyclopropaneacetic acid

A 100 ml 3-necked flask fitted with a thermometer and a condenser mounted with a nitrogen inlet was charged with 10 g of 1-(isothiuroniummethyl)cyclopropane-acetonitrile hydrobromide (0.04 mol) and 38.3 ml of 20% degassed sodium hydroxide solution. The mixture was stirred and heated to reflux for about 14 hours under nitrogen atmosphere. Upon cooling to room temperature, degassed ethyl acetate was added to the mixture, which was then cooled to –5~5° C. The mixture was neutralized with degassed 85% formic acid until a pH value in the range of 3.5-4.0 was obtained. The organic layer was separated and the aqueous layer was further extracted with degassed ethyl acetate. The combined organic layers were washed with degassed water, dried and concentrated to give the crude 1-(mercaptomethyl)cyclopropane-acetic acid, which was purified by crystallization from hexanes. After drying under vacuum, 4.48 g of 1-(mercaptomethyl)cyclopropaneacetic acid was obtained as a white solid, in 76.7% yield, having a purity of 97.9%.

Example 4

Preparation of montelukast acid cyclohexyl ammonium salt

A 500 ml 3-necked flask equipped with a thermometer, a nitrogen inlet and a magnetic stirrer was charged at room temperature with 1.8 g (0.0123 moles) of 1-(mercaptomethyl)cyclopropaneacetic acid and 16 ml of DMF under stirring and under nitrogen atmosphere to obtain a solution. 1.8 ml of NaOH 47% (0.032 moles) was added drop-wise and stirring was maintained for 10 minutes to afford a suspension. A solution of 3 g of the mesylate XIV in 20 ml THF was added in portions at 25° C. After completing the addition, the mixture was stirred for 2 hours at 25° C. and reaction completion was checked by HPLC. 43 ml of ethyl acetate was added to the reaction mixture and 43 ml of 5% sodium chloride solution. The mixture was stirred at 25° C. for 15 minutes. Then, the layers were separated and 28 ml of 0.5 M tartaric acid was added to the upper layer and stirring was maintained at 25° C. for 15 minutes. The layers were separated and the upper layer was washed with 14 ml of water and again separated. The organic layer was distilled to dryness to afford an oily residue. 34 ml of ethyl acetate was added to the residue and the mixture was distilled off to dryness to afford 3.8 g of an oily residue. 34 ml of ethyl acetate was added to the residue under stirring to obtain a solution. 0.8 ml of cyclohexylamine was added and stirring was maintained for few minutes at 25° C. and the solution was seeded with crystalline montelukast acid cyclohexyl ammonium salt. Stirring was maintained at 25° C. to afford a suspension, which was filtered to obtain a cake. The cake was washed with ethyl acetate and dried at 40° C. in vacuum to afford 2.7 g of dry crude montelukast acid cyclohexyl ammonium salt in 65% yield. The HPLC purity was 95%.

What is claimed is:

1. An acid addition salt of 1-(isothiuroniummethyl)cyclopropaneacetonitrile, having the structural formula

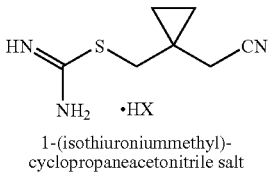

1-(isothiuroniummethyl)-
cyclopropaneacetonitrile salt wherein X represents a halogen atom.

2. The salt compound of claim 1, wherein X is a Br atom.
3. The salt compound of claim 1, which is in crystalline form.

* * * * *